(12) United States Patent
Jeong

(10) Patent No.: US 11,752,187 B2
(45) Date of Patent: Sep. 12, 2023

(54) ANTI-OBESITY COMPOSITION INCLUDING GEUMHWAGYU EXTRACT AS ACTIVE INGREDIENT

(71) Applicant: Andong National University Industry-Academic Cooperation Foundation, Andong-si (KR)

(72) Inventor: Jin-Boo Jeong, Andong-si (KR)

(73) Assignee: Andong National University Industry-Academic Cooperation Foundation, Andong-si (KR)

( * ) Notice: Subject to any disclaimer, the term of this patent is extended or adjusted under 35 U.S.C. 154(b) by 70 days.

(21) Appl. No.: 17/577,053

(22) Filed: Jan. 17, 2022

(65) Prior Publication Data
US 2022/0354918 A1   Nov. 10, 2022

(30) Foreign Application Priority Data
May 4, 2021   (KR) .......................... 10-2021-0057807

(51) Int. Cl.
*A61K 36/73*   (2006.01)
*B01D 11/04*   (2006.01)

(52) U.S. Cl.
CPC .......... *A61K 36/73* (2013.01); *B01D 11/0492* (2013.01)

(58) Field of Classification Search
None
See application file for complete search history.

(56) References Cited

FOREIGN PATENT DOCUMENTS

| KR | 10-2017-0029328 A | 3/2017 |
|---|---|---|
| KR | 10-2020-0120465 A | 10/2020 |
| KR | 10-2176935 B1 | 11/2020 |
| KR | 10-2020-0137522 A | 12/2020 |
| KR | 10-2021-0033422 A | 3/2021 |

OTHER PUBLICATIONS

Jong Kug Lee et al., "Screening of Medicinal Plants containing Lipase Inhibitor and Optimal Extraction Conditions", Korean J. Medicinal Crop Sci, 2012, vol. 20, No. 1, pp. 1-7.

*Primary Examiner* — Michael V Meller
(74) *Attorney, Agent, or Firm* — You & IP, LLC

(57) ABSTRACT

Proposed is a Geumhwagyu extract as an active ingredient. The Geumhwagyu extract of the present disclosure inhibits the differentiation of pre-adipocytes by inducing the degradation of CEBP-α and inhibits the expression of CEBP-α, PPARγ, Perilipin-1, Adiponectin, FABP4, etc., to suppress the accumulation of lipids in adipocytes. It can be easily used as a composition for preventing or managing obesity by inhibiting it and lowering the content of TG (Triacylglycerol) to show anti-obesity activity.

1 Claim, 5 Drawing Sheets

ANTI-OBESITY COMPOSITION INCLUDING GEUMHWAGYU EXTRACT AS ACTIVE INGREDIENT

CROSS REFERENCE TO RELATED APPLICATION

The present application claims priority to Korean Patent Application No. 10-2021-0057807, filed May 4, 2021, the entire contents of which is incorporated herein for all purposes by this reference.

BACKGROUND OF THE INVENTION

1. Field of the Invention

The present disclosure relates to an anti-obesity composition including Geumhwagyu (*Hibiscus manihot* L.) extract as an active ingredient.

2. Description of the Related Art

Obesity refers to a medical condition in which body fat is excessively accumulated to the extent that it may have a negative effect on health. When the number of calories consumed from food exceeds the number of calories consumed through physical activity, it is stored as body fat. Obesity is when men have more than 25% body fat, and women have more than 30% body fat. Obesity is a condition in which fat is excessively accumulated in the body and is a risk factor that causes various adult diseases as well as appearance problems. Obesity is a cause of fatty liver, hyperlipidemia, osteoarthritis, cholelithiasis, hypertension, diabetes, and cardiovascular disease. In addition, it is known that prostate cancer, rectal cancer, and colorectal cancer are associated with obesity in men, and breast cancer, ovarian cancer, and uterine cancer are associated with obesity in women. In particular, obesity is a significant risk factor for heart disease, and it has been reported that obesity can significantly affect the structure and function of the heart. As it is known that the risk of heart failure increases rapidly with obesity in childhood, it is becoming an important problem in health care to solve obesity. The causes of obesity include diseases such as abnormalities in hypothalamic function and energy metabolism, and genetic factors, but most obesity is caused by lifestyle habits caused by excessive nutritional intake and a decrease in the amount of physical activity. In recent years, the incidence of obesity has continued to increase due to the increase in consumption of instant foods and lack of exercise due to western-style eating patterns and convenience of life. It is predicted that this trend will become more severe as time goes by. Recently, obesity has been socially recognized as a disease, and various pharmaceutical companies are focusing their efforts on developing drugs that treat obesity. The fat absorption inhibitor Xenical™ (Roche Pharmaceuticals, Switzerland) is one of the most used obesity treatments worldwide. Orlistat, a component of Xenical, combines with digested fat to suppress absorption in the intestine, thereby excreting some of the fat components during digesting. Other drugs developed include Riductil™ (Avot, USA) and Exolise™ (Atopharma, France), which enhance satiety. However, the commercialized drugs have reported side effects, including liver damage, gastrointestinal bleeding, pancreatitis, and kidney stones, and there is a risk of developing heart disease, respiratory disease, and nervous system diseases. Therefore, when using the currently commercialized anti-obesity treatments, it is required to develop a material having fewer side effects and excellent anti-obesity effects due to problems such as stability as described above.

Geumhwagyu (*Hibiscus manihot* L.) is a medicinal plant, such as roots, stems, leaves, and flowers, with medicinal properties and is a valuable medicinal herb that can only be obtained during the July-August harvest. Geumhwagyu is rich in collagen, which is effective for skin beauty, and contains a large number of effective ingredients such as palmitic acid, Gossypetin, oleic acid, betaine, and linolenic acid, so it is in the spotlight as a flower tea.

Accordingly, the present inventors completed the present disclosure by confirming that the Geumhwagyu extract has an anti-obesity effect while studying various physiological activities of the Geumhwagyu extract.

DOCUMENTS OF RELATED ART (Patent Document 0001) Korea Patent Application Publication No. 10-2020-0120465 (Title of the disclosure: Composition for preventing or treating liver damage caused by alcohol and for effectively relieving hangover, Applicant: Solgo Biomedical Co., Ltd., release date: Oct. 21, 2020)

(Patent Document 0002) Korea Patent No. 10-2176935 (Title of the disclosure: Cosmetic composition for wrinkle improvement and anti-inflammatory, Applicant: Jong-bok Kwak, date of registration: Nov. 4, 2020)

SUMMARY OF THE INVENTION

The objective of the present disclosure is to provide an anti-obesity composition including Geumhwagyu (*Hibiscus manihot* L.) extract as an active ingredient.

The present disclosure relates to an anti-obesity composition including Geumhwagyu (*Hibiscus manihot* L.) extract as an active ingredient.

The Geumhwagyu extract may be flowers, stems, leaves, or root extracts of Geumhwagyu. In addition, the Geumhwagyu extract may be extracted using water, C1 to C4 alcohol, or a mixed solution thereof as a solvent. The Geumhwagyu extract may be a filtrate obtained by adding Geumhwagyu to water, C1 to C4 alcohol, or a mixed solution thereof, stirring at 20° C. to 30° C. for 1 to 5 days, and filtering the extract. Preferably, the extract may be a filtrate filtered after adding Geumhwagyu to water, C1 to C4 alcohol, or a mixed solution thereof, stirring at 20° C. to 30° C. for 3 to 5 days. Most preferably, the Geumhwagyu extract may be a filtrate filtered after adding Geumhwagyu to water, C1 to C4 alcohol, or a mixed solution thereof, stirring at 25° C. for 5 days. The Geumhwagyu extract may be treated at an effective concentration of 10 µg/ml to 200 µg/ml to be used as an anti-obesity composition, preferably 10 µg/ml to 100 µg/ml, more preferably 50 µg/ml to 100 µg/ml. The C1 to C4 alcohol may be selected from the group consisting of methanol, ethanol, propanol, isopropanol, butanol, and isobutanol.

The filtrate may be dried and powdered and may be powdered through conventional drying methods such as freeze-drying, hot air drying, spray drying, and the like.

In addition, as a conventional method in the art, after dissolving the Geumhwagyu extract extracted from water, C1 to C4 alcohol or a mixture solution thereof in water, the Geumhwagyu extract may be further fractionated using at least one solvent selected from the group consisting of n-hexane, methylene chloride, acetone, chloroform, ethyl acetate, and n-butanol to prepare a fraction.

In another method, after suspension by adding water to the Geumhwagyu extract obtained by extracting and concentrating Geumhwagyu with water, C1 to C4 alcohol, or a mixed solvent thereof, preferably 1 to 1000 times the weight of the Geumhwagyu extract, more preferably 1 to 500 times, and most preferably 1 to 50 times the weight of the Geumhwagyu extract. Then the Geumhwagyu extract may be prepared as a Geumhwagyu fraction obtained by adding a solvent selected from the group consisting of hexane, chloroform, ethyl acetate, and butanol to the suspension. The Geumhwagyu fraction may preferably be: a hexane layer concentrate obtained by mixing hexane to Geumhwagyu extract by extracting and concentrating Geumhwagyu with water, C1 to C4 alcohol, or a mixed solvent thereof, and making a suspension in water; a chloroform layer concentrate obtained by mixing chloroform with the residue (water layer) remaining after removing the hexane layer; an ethyl acetate layer concentrate obtained by mixing ethyl acetate with the residue (water layer) remaining after removing the chloroform layer; a butanol layer concentrate obtained by mixing butanol with the residue (water layer) remaining after removing the ethyl acetate layer; or a remaining residue (water layer) concentrate after removing the butanol layer. On the other hand, other fractionation conditions are not limited, but a suspension may be prepared by adding water of 1 to 50 times the weight of the Geumhwagyu extract to the Geumhwagyu extract, and then fractionated by adding a solvent selected from the group consisting of hexane, chloroform, ethyl acetate, and butanol equivalent to the water. In addition, even when chloroform is added to the remaining residue after removing the hexane layer, when ethyl acetate is added to the remaining residue after removing the chloroform layer, and when butanol is added to the remaining residue after removing ethyl acetate, and also even when it is performed in stages, each solvent (chloroform, ethyl acetate, or butanol) equivalent to the residue can be sequentially added and fractionated.

It is preferable to use water rather than an organic solvent to extract the Geumhwagyu extract.

As an apparatus for extracting the Geumhwagyu extract or fractions, a conventional extraction apparatus, an ultrasonic crushing extractor, or a fractionator may be used. The thus-prepared Geumhwagyu extract may be dried with hot air, dried under reduced pressure, or freeze-dried to remove the solvent. In addition, the Geumhwagyu extract or fraction may be purified and used using column chromatography.

The Geumhwagyu extract may be used by fractioning or purifying using the known method alone or a suitably combined method used for separation and extraction of plant components, such as extraction by an organic solvent (alcohol, ether, acetone, etc.), distribution of hexane, and water, and method by column chromatography, according to the commercial method.

The chromatography may be selected from silica gel column chromatography, LH-20 column chromatography, ion exchange resin chromatography, medium pressure liquid chromatography, thin-layer chromatography (TLC), silica gel vacuum liquid chromatography, and high-performance liquid chromatography.

In addition, the present disclosure provides a pharmaceutical composition for anti-obesity containing Geumhwagyu extract. The Geumhwagyu extract may be added to the pharmaceutical composition of the present disclosure in an amount of 0.001% to 100% by weight.

The pharmaceutical composition may be formed in the form of oral formulations such as powders, granules, tablets, capsules, suspensions, emulsions, syrups, aerosols, etc., external preparations, suppositories, and sterile injection solutions according to conventional methods, respectively. Carriers, excipients, and diluents that may be included in the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, and mineral oil. In the case of formulation, it is prepared using commonly used fillers, extenders, binders, wetting agents, disintegrants, diluents such as surfactants or excipients. Solid preparations for oral administration include tablets, pills, powders, granules, capsules, etc. These solid preparations are prepared by mixing at least one excipient, for example, starch, calcium carbonate, sucrose or lactose, and gelatin, etc. In addition to simple excipients, lubricants such as magnesium stearate and talc are also used. Liquid formulations for oral administration include suspensions, solutions, emulsions, syrups, etc. In addition to water and liquid paraffin, which are commonly used simple diluents, various excipients, for example, wetting agents, sweeteners, fragrances, preservatives, etc., may be included. Formulations for parenteral administration include sterile aqueous solutions, non-aqueous solutions, suspensions, emulsions, freeze-dried preparations, and suppositories. Vegetable oils such as propylene glycol, polyethylene glycol, and olive oil and injectable esters such as ethyl oleate may be used as non-aqueous solvents and suspensions. As the base of the suppository, Witepsol, Macrogol, Tween 61, cacao butter, laurin butter, glycerogelatin, etc., can be used.

The dosage of the pharmaceutical composition of the present disclosure will vary depending on the age, gender, weight, specific disease or pathology to be treated, severity of the disease or pathology to be treated, the route of administration, and the prescription's judgment. Dosage determination based on these factors is within the level of those of ordinary skilled in the art. Generally, dosages range from 0.01 mg/kg/day to approximately 2000 mg/kg/day. A more preferred dosage is 1 mg/kg/day to 500 mg/kg/day. Administration may be administered once a day or may be administered in several divided doses. The above dosage does not limit the scope of the present disclosure in any way.

The pharmaceutical composition of the present disclosure may be administered to mammals such as mice, livestock, and humans by various routes. Any mode of administration can be envisaged, for example, by oral, rectal or intravenous, intramuscular, subcutaneous, intrauterine dural, or intracerebrovascular injection. Since the extract of the present disclosure has almost no toxicity and side effects, it is a drug that can be safely used even when taken for a long time for prevention.

In addition, the present disclosure provides healthy functional food for anti-obesity, including a Geumhwagyu extract and a food additive that is acceptable in terms of food. The Geumhwagyu extract may be added to the health functional food of the present disclosure in an amount of 0.001% to 100% by weight. The healthy functional food of the present disclosure includes the form of tablets, capsules, pills, or liquids, and the food to which the extract of the present disclosure can be added includes, for example, various drinks, meat, sausage, bread, candy, snacks, noodles, ice cream, dairy products, soups, ionized beverages, beverages, alcoholic beverages, gum, tea, and vitamin complexes.

The present disclosure relates to an anti-obesity composition, including Geumhwagyu extract as an active ingredient. The Geumhwagyu extract inhibits the differentiation of pre-adipocytes by inducing the degradation of CEBP-α and suppresses the expression of CEBP-α, PPARγ, Perilipin-1, Adiponectin, FABP4, etc., to suppress the accumulation of lipids in adipocytes. Therefore, the Geumhwagyu extract can be easily used as a composition for preventing or managing obesity by showing anti-obesity activity by lowering the content of triacylglycerol (TG).

DESCRIPTION OF THE PREFERRED EMBODIMENTS

Figure 1:
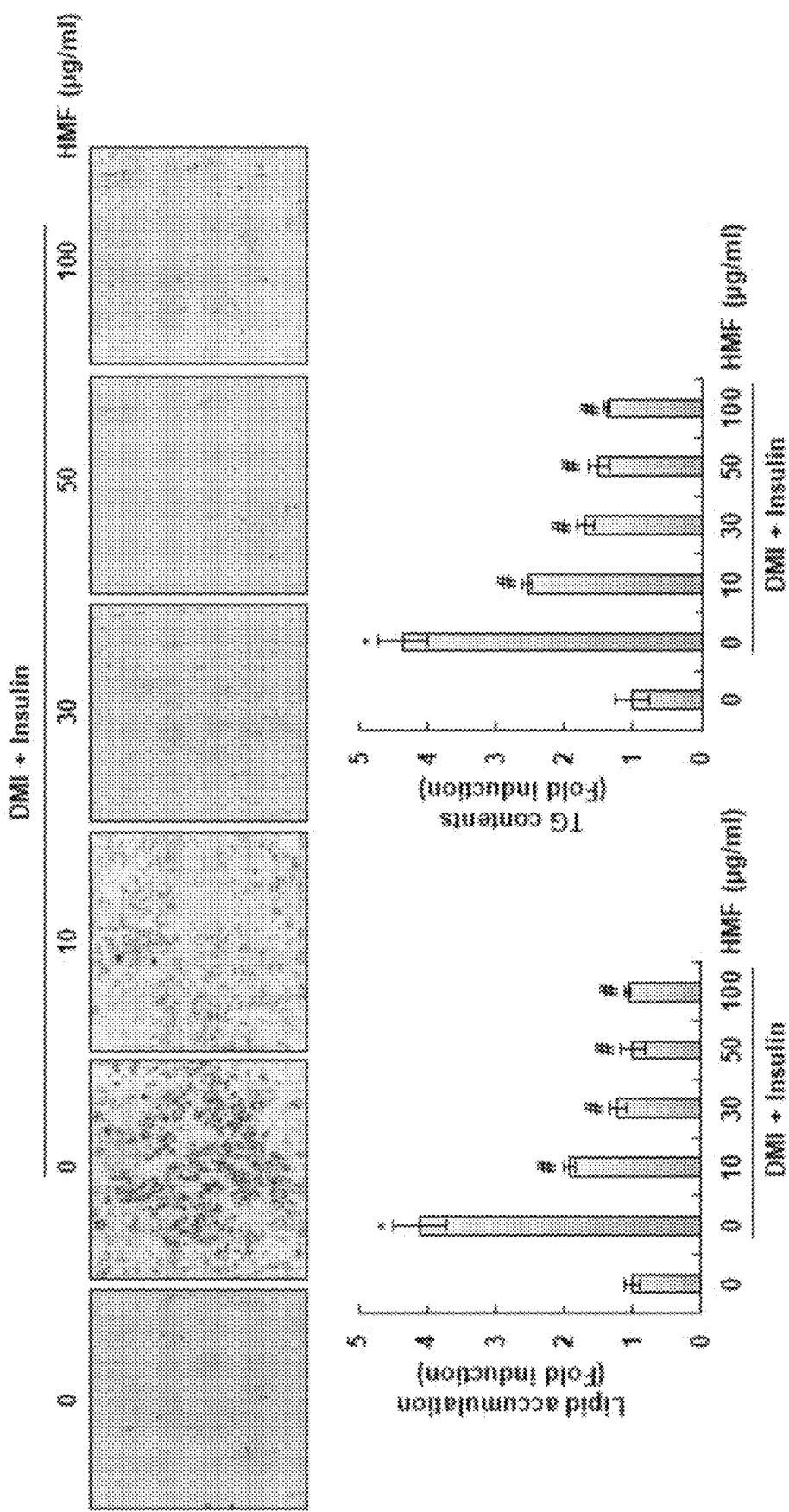
FIG. 1 is a graph showing a cell image for lipid accumulation according to an Oil Red O experiment of a Geumhwagyu flower extract (HMF), and an absorbance result of a cell eluate, and a TG synthesis result according to TG measurement.

Hereinafter, preferred embodiments of the present disclosure will be described in detail.

However, the present disclosure is not limited to the embodiments described herein and may be embodied in other forms. Rather, it is provided so that this disclosure will be thorough and complete and will fully convey the spirit of the disclosure to those skilled in the art.

Example 1: Preparation of Geumhwagyu Extract

Geumhwagyu flower, leaf, stem, and root extracts were prepared through the following process. First, the flowers, leaves, stems, and roots of Geumhwagyu grown by E-Farm Co., Ltd., an agricultural company located in Punggi, Gyeongsangbuk-do, Korea, were washed thoroughly with distilled water and dried. Water equivalent to 20 times the volume of the dry pulverized product was added to 10 g of dry pulverized product and stirred at room temperature of 25° C. for 3 days to obtain each of the Geumhwagyu flower, leaf, stem, and root extract. Thereafter, the extract was filtered and then freeze-dried to obtain the final extracts of Geumhwagyu flowers (HMF), leaves (HMF), stems (HMF), and roots (HMF).

Example 2: Cytotoxicity Assay

In order to check whether the Geumhwagyu extract of the present disclosure obtained in Example 1 is toxic to cells, cytotoxicity was analyzed in vitro.

To this end, 3T3-L1, a pre-adipocyte, was purchased from KCLB and used. After the cells were aliquoted in a cell culture flask, 10% fetal bovine serum (FBS) and 1% penicillin-streptomycin (10,000 U/ml) were added to the DMEM medium and cultured and used in an incubator maintained at 37° C., 5% $CO_2$, and 95% humidity conditions. For cytotoxicity evaluation, the MTT assay was used, in which the method uses a principle that dehydrogenases in mitochondria of cells with intact metabolic processes reduce yellow water-soluble tetrazolium salt [3-(4,5-dimethylthiazol-2-yl)-2-5-diphenyltrazolium bromide] (MTT) to non-soluble dark purple MTT formazan crystals. The crystal was evaluated for cytotoxicity by measuring absorbance at an appropriate wavelength (mainly 500-600 nm).

First, 3T3-L1 cells were aliquoted into 96 wells at a 1×105 cells/well concentration, and then cultured for 24 hours. Then, each part of the extract of Geumhwagyu prepared in Example 1 was treated at a concentration of 0, 50, 100, and 200 μg/mL, respectively, and after incubation for 24 hours, MTT at a concentration of 1 mg/mL was added and incubated at 37° C. for 2 hours. After the reaction, DMSO (dimethyl sulfoxide) was added, and absorbance was measured at 570 nm using a microplate reader.

As a result of the analysis, it was confirmed that all Geumhwagyu extracts had no cytotoxicity, and then the following experiment was performed (graph not attached).

Example 3: Activity of Inhibiting Lipid Accumulation and Triglyceride (TG) Production of Geumhwagyu Extract 3T3-L1 cells, which are pre-adipocytes, were aliquoted into 96 wells at a 1×105 cells/well concentration and cultured for 3 days and then differentiated with the DMI medium (adipogenic medium). As the MDI medium, 10% FBS/DMEM treated with 0.5 mM of IBMX, 1 μM dexamethasone, and 1 μg/ml insulin was used. This time point was regarded as day 0 of differentiation, and after 2 days of differentiation, 1 μg/ml of insulin medium was replaced, and after 2 days of culture, 10% FBS medium was replaced and maintained for up to 8 days. Geumhwagyu extract was added on day 0 of differentiation and treated for 8 days. After 8 days of differentiation, the degree of differentiation of adipocytes and the degree of inhibition of differentiation by Geumhwagyu extract were analyzed through Oil Red O staining. After adipocyte differentiation and Geumhwagyu extract treatment were completed, cells were washed with 1× phosphate-buffered saline (PBS), and then 10% (w/v) formalin was added and fixed at room temperature for 1 hour. After removing the formalin and washing each well in which the cells were cultured with 60% (v/v) isopropanol, the isopropanol was completely blown away from the hood. Oil red O solution was added to the dried cell culture wells, left for 10 minutes, washed with distilled water, and adipocyte differentiation was confirmed by microscopic imaging. The stained cell culture wells were dissolved in 100% isopropanol, and absorbance was measured at 500 nm. The triglyceride (TG) amount in adipocytes was measured using a commercially available TG assay kit (Triglyceride Assay Kit Quantification, ab65336). The results of each experiment are shown in FIGS. 1 to 4.

Figure 2:
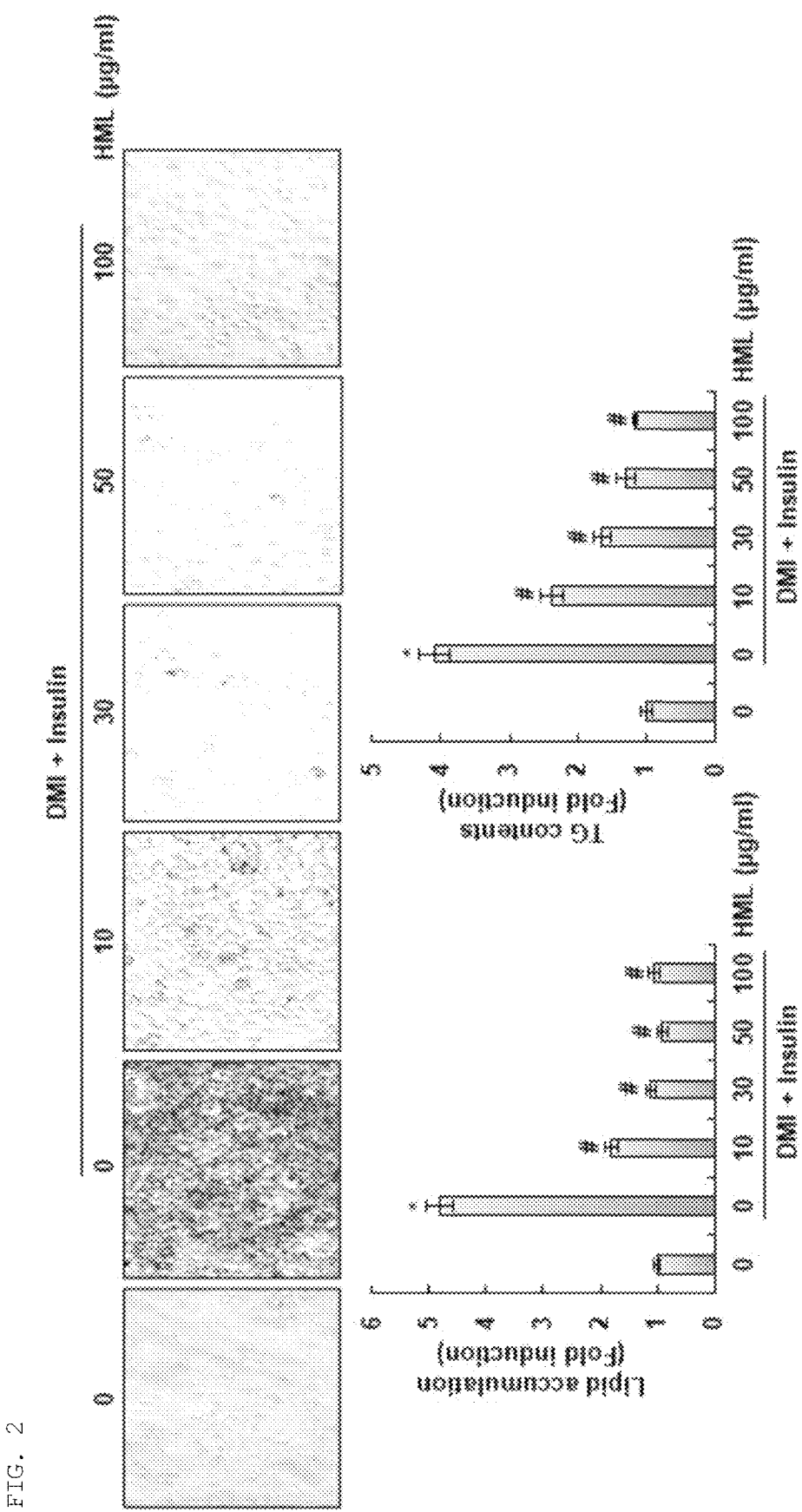
FIG. 2 is a graph showing a cell image for lipid accumulation according to the Oil Red O experiment of a Geumhwagyu leaf extract (HMF), and an absorbance result of the cell eluate, and a TG synthesis result according to TG measurement.
Figure 3:
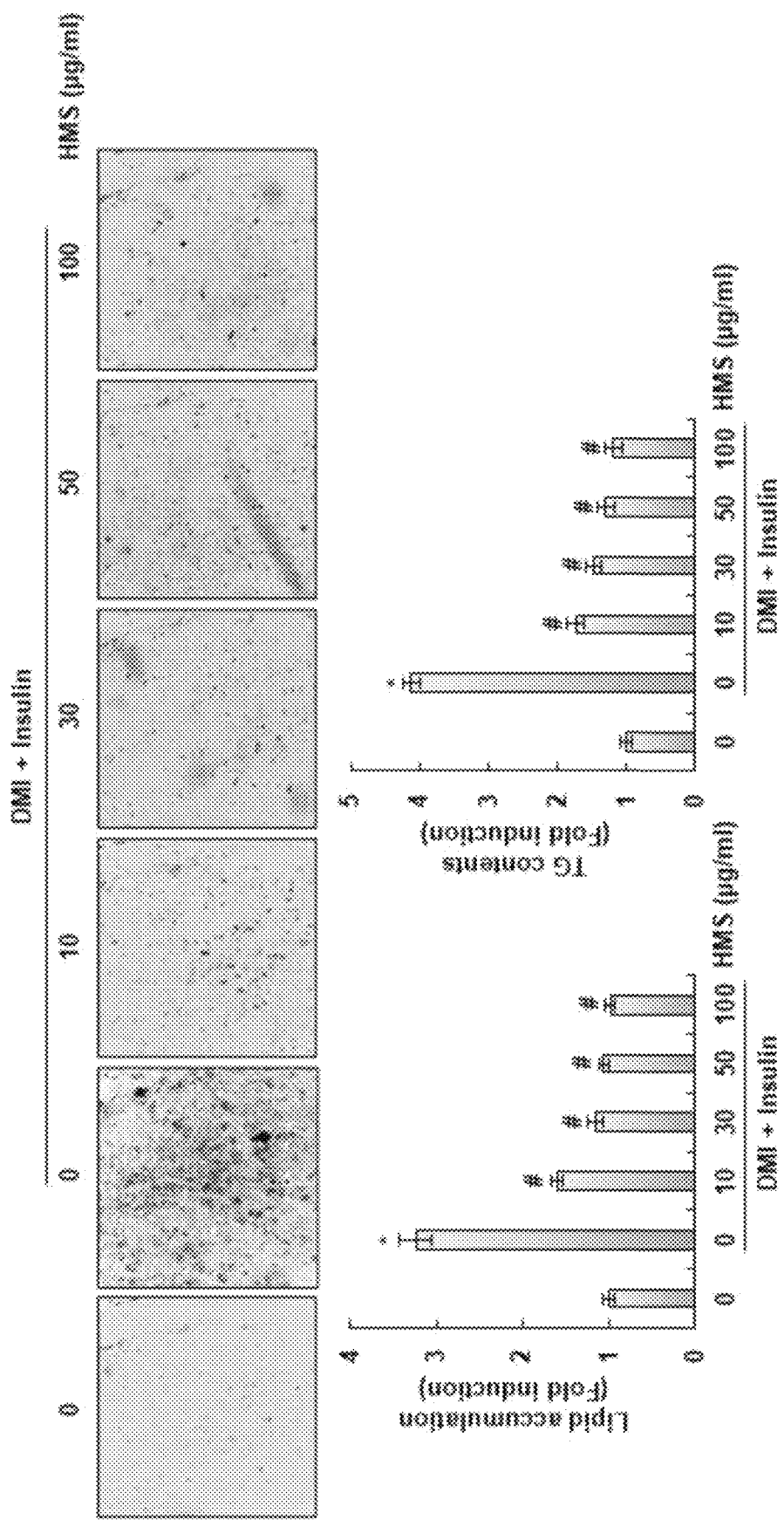
FIG. 3 is a graph showing a cell image for lipid accumulation according to the Oil Red O experiment of Geumhwagyu stem extract (HMF), and an absorbance result of the cell eluate, and a TG synthesis result according to TG measurement.
Figure 4:
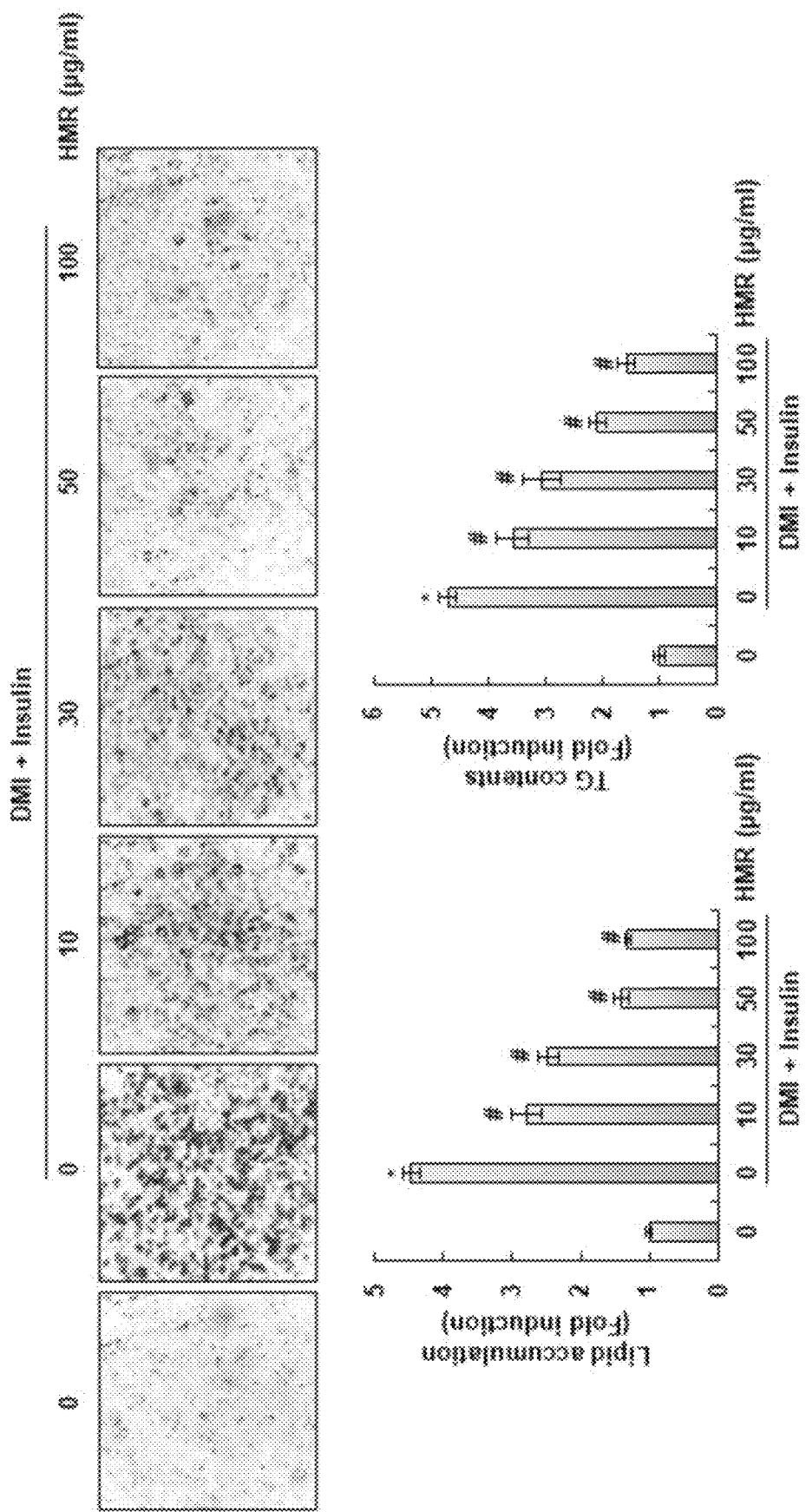
FIG. 4 is a graph showing a cell image for lipid accumulation according to the Oil Red O experiment of Geumhwagyu root extract (HMF), and an absorbance result of the cell eluate, and a TG synthesis result according to TG measurement.

The results of the Geumhwagyu flower extract (HMF) are described in FIG. 1, the Geumhwagyu leaf extract (HML) in FIG. 2, the Geumhwagyu stem extract (HMS) in FIG. 3, and the Geumhwagyu root extract (HMR) in FIG. 4.

Referring to FIGS. 1 to 4, it can be confirmed that the lipid accumulation is suppressed through the cell image and the absorbance result of the cell eluate, which are the results of the Oil Red O experiment, of the extracts for each part of Geumhwagyu, and the content of triglyceride (TG) produced and accumulated in cells is also significantly reduced.

Example 3: Inhibitory Activity of Lipid Accumulation-Related Protein Expression of Geumhwagyu Extract 3T3-L1 cells, which are pre-adipocytes, were aliquoted in a 24-well culture at a 1×105 cells/well concentration and cultured for 3 days and then differentiated with MDI medium. This time point was regarded as day 0 of differentiation, and after 2 days of differentiation, 1 µg/ml of insulin medium was replaced, and after 2 days of culture, 10% FBS medium was replaced and maintained for up to 8 days. Geumhwagyu extract was added on day 0 of differentiation and treated for 8 days. After 8 days of differentiation, cells were harvested, and the expression of lipid accumulation-related proteins was investigated through Western blot analysis.

Figure 5:
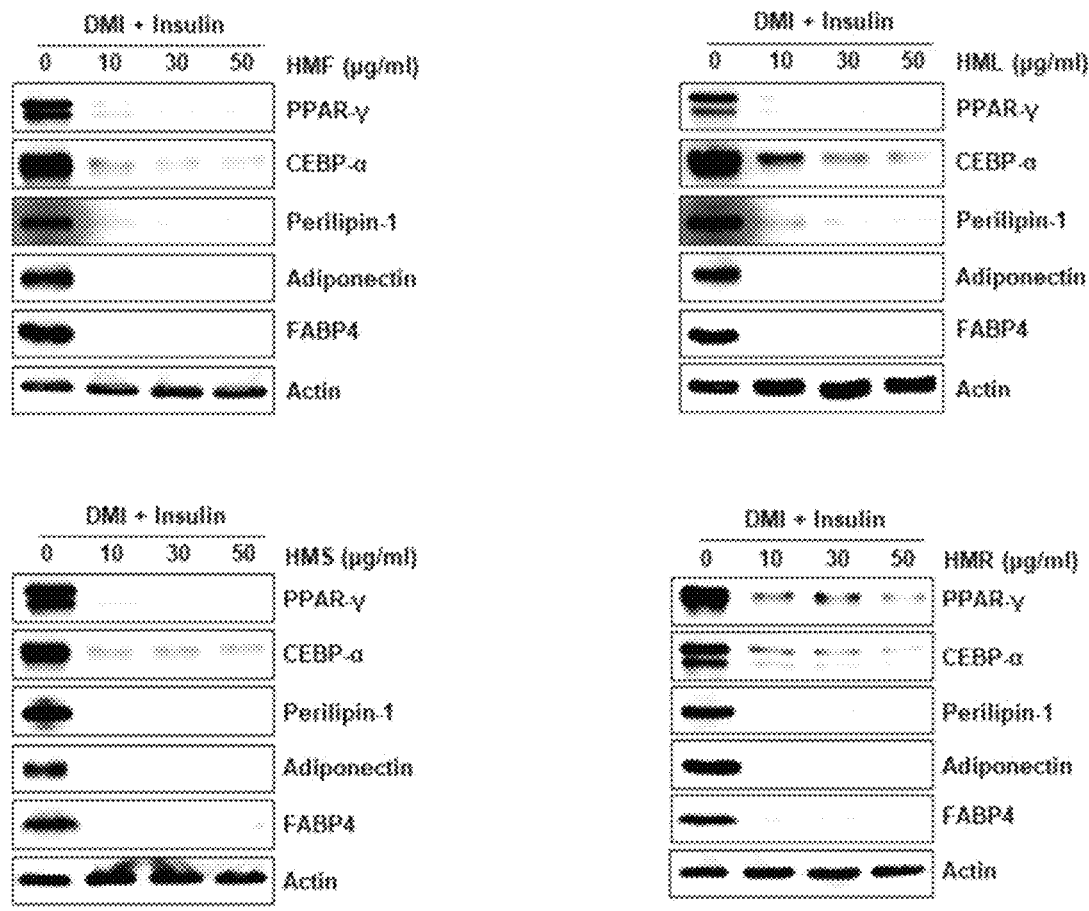
FIG. 5 is a Western blot resulting image showing inhibition of expression of PPARγ, CEBPα, Perilipin-1, Adiponectin, FABP4, etc., which are proteins related to lipid accumulation of Geumhwagyu flowers (HMF), leaves (HMF), stems (HMF), and roots (HMF) extracts.

FIG. 5 is a Western blot image showing lipid accumulation-related protein expression regulation of Geumhwagyu flower (HMF), leaf (HML), stem (HMS), and root (HMR) extracts. It was shown to inhibit the expression of adipocyte lipids accumulation-related proteins, such as PPARγ, CEBPα, Perilipin-1, Adiponectin, and FABP4.

Through these results (FIGS. 1 to 5), it can be verified that the extracts of Geumhwagyu flowers, leaves, stems, and roots have anti-obesity activity by inhibiting the expression of lipid accumulation-related proteins in adipocytes.

Formulation Example 1. Pharmaceutical Preparations 200 g of the extract for each part of the flowers, stems, leaves, or roots of Geumhwagyu of the present disclosure was mixed with 175.9 g of lactose, 180 g of potato starch, and 32 g of colloidal silicic acid. After adding a 10% gelatin solution to this mixture, it was ground and passed through a 14 mesh sieve. This was dried, and 160 g of potato starch, 50 g of talc, and 5 g of magnesium stearate were added thereto, and the resulting mixture was made into tablets.

Formulation Example 2. Food Manufacturing

Formulation Example 2-1. Preparation of Cooking Condiments

Cooking condiments for health promotion were prepared by adding the extract of each part of the flowers, stems, leaves, or roots of Geumhwagyu of the present disclosure to the cooking condiments at 1% by weight.

Formulation Example 2-2. Flour Food Manufacturing

The extract for each part of the flowers, stems, leaves, or roots of Geumhwagyu of the present disclosure is added to wheat flour in an amount of 0.1% by weight, and the mixture is used to prepare bread, cake, cookies, crackers, and noodles to produce health-promoting food.

Formulation Example 2-3. Preparation of Soup and Gravies

The extract of each part of the flowers, stems, leaves, or roots of Geumhwagyu of the present disclosure was added to soup and gravies in an amount of 0.1% by weight to prepare health-promoting soup and gravies.

Formulation Example 2-4. Manufacture of Dairy Products

The extract of each part of the flowers, stems, leaves, or roots of Geumhwagyu of the present disclosure was added to milk in an amount of 0.1% by weight, and various dairy products such as butter and ice cream were prepared using the milk.

Formulation Example 2-5. Vegetable Juice Production

Vegetable juice for health promotion was prepared by adding 0.5 g of the extract of each part of the flowers, stems, leaves, or roots of Geumhwagyu of the present disclosure to 1,000 ml of tomato juice or carrot juice.

Formulation Example 2-6. Fruit Juice Manufacturing

Fruit juice for health promotion was prepared by adding 0.1 g of the extract for each part of the flowers, stems, leaves, or roots of Geumhwagyu of the present disclosure to 1,000 ml of apple juice or grape juice.

What is claimed is:
1. A tablet consisting essentially of a *Hibiscus Manihot* extract, polyvinyl pyrrolidone and microcrystalline cellulose.

* * * * *